Figure 1:
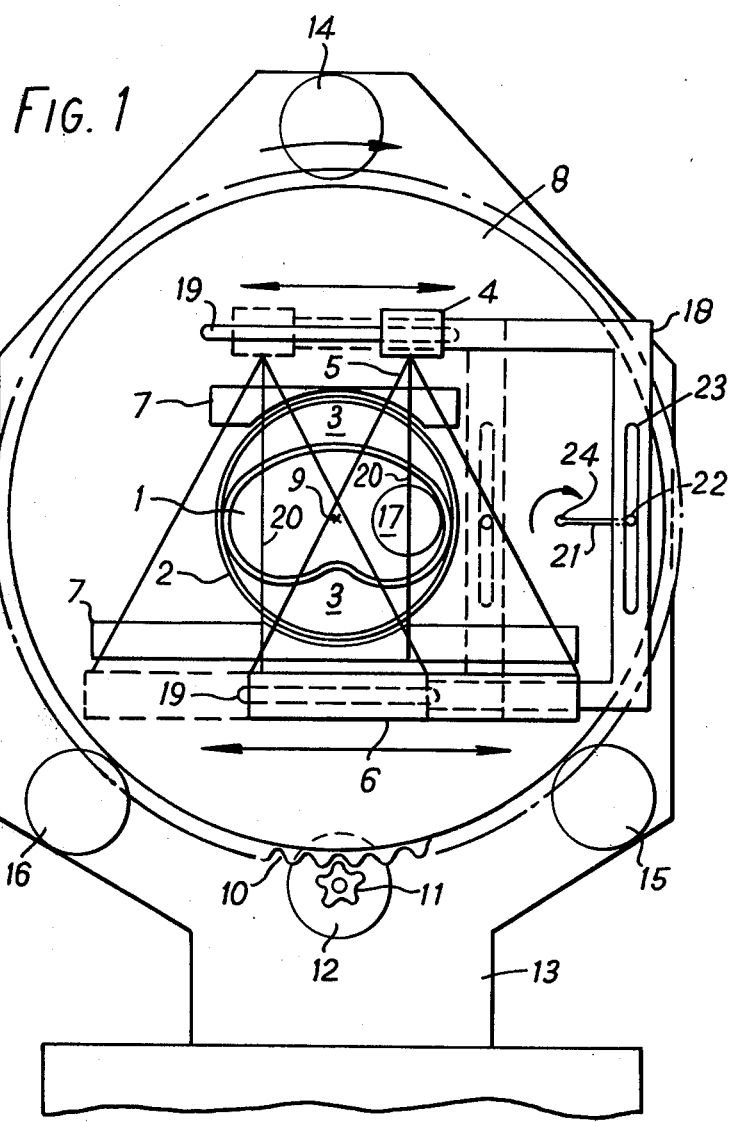

United States Patent [19]

Hounsfield

[11] 4,114,040
[45] Sep. 12, 1978

[54] RADIOGRAPHY

[75] Inventor: Godfrey Newbold Hounsfield, Newark, England

[73] Assignee: EMI Limited, Hayes, England

[21] Appl. No.: 655,396

[22] Filed: Feb. 5, 1976

[30] Foreign Application Priority Data

Feb. 8, 1975 [GB] United Kingdom ............... 5441/75

[51] Int. Cl.² ........................................... G03B 41/16
[52] U.S. Cl. .................................. 250/445 T; 250/490
[58] Field of Search ................... 250/445 T, 360, 363, 250/366, 490

[56] References Cited

U.S. PATENT DOCUMENTS 3,937,963  2/1976  Hounsfield ..................... 250/445 T
3,946,234  3/1976  Hounsfield ..................... 250/445 T

FOREIGN PATENT DOCUMENTS 2,521,889  11/1975  Fed. Rep. of Germany ....... 250/445 T Primary Examiner—Craig E. Church
Attorney, Agent, or Firm—Cooper, Dunham, Clark, Griffin & Moran

[57] ABSTRACT

In computerized axial tomographic apparatus, arranged to provide an image of the variation of absorption coefficient over a planar slice of a patient's body, means are described for permitting a region of particular interest, within said slice, to be investigated in detail. To this end, the body is irradiated with a spread of radiation in the plane of said slice, the spread being rotated around the body. During the rotation the median line of the spread is not generally concurrent with the axis of rotation, but instead is preferably concurrent with the center of said region of particular interest.

12 Claims, 2 Drawing Figures

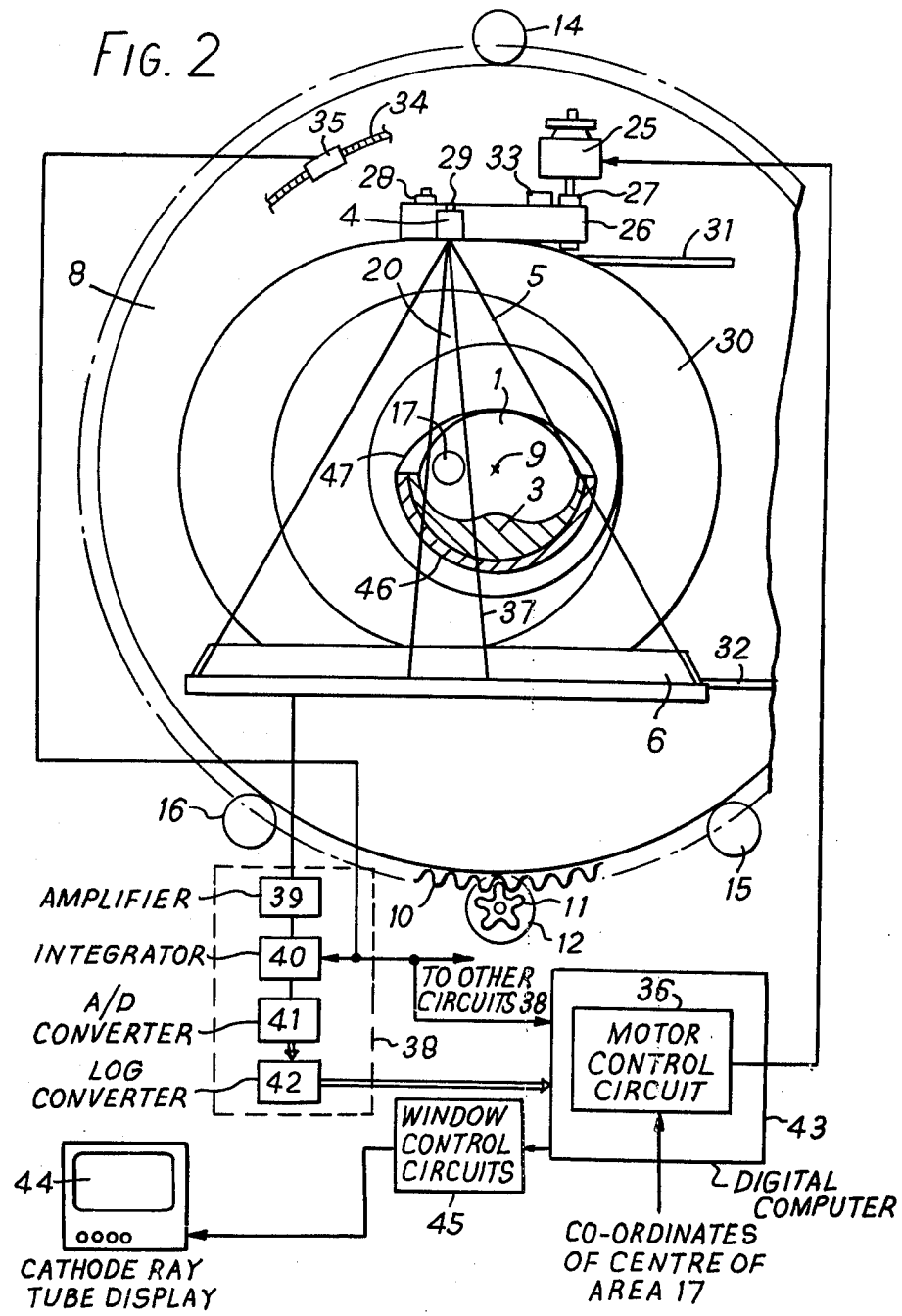

RADIOGRAPHY

The present invention relates to radiography, and it relates especially to apparatus for scanning a body, or a part thereof, with penetrating radiation such as X-radiation so as to provide information indicative of the absorption suffered by the radiation on traversing many substantially linear paths through the body in a plane. The information can be processed to evaluate the absorption coefficient, with respect to the radiation used, in each element of a two-dimensional array of elements distributed over the irradiated plane of the body.

It has been disclosed, for example in U.S. Pat. No. 3,778,614 that in order to effect rapid scanning of the body it is convenient to utilise a source of radiation which provides a planar, fan-shaped spread of the radiation rather than a single pencil-like beam. The source, together with associated detector means, is scanned relative to the body in order to provide sufficient information to permit the aforementioned coefficients to be accurately evaluated. Such scanning involves, in the examples described in the aforementioned U.S. Pat. No. 3,778,614 lateral scanning movements of the detector means as well as rotational movements of both the source and the detector means about an axis perpendicular to the plane of the spread of radiation.

As described, for example in U.S. Pat. No. 3,937,963 more rapid scanning can be effected if the spread of radiation is sufficiently broad to encompass substantially the whole of the breadth of the body in the irradiated plane. The lateral scanning movements referred to above can thus be dispensed with; the scanning movement then comprising only a rotational movement.

It has been disclosed in U.S. application Ser. No. 493,403, filed on July 31, 1974, that it is not necessary for the information derived across the entire width of the spread to be of the same resolution. In particular, the resolution can be degraded towards the extremities of the spread as compared with the resolution at the centre of the spread. The accuracy of evaluation of the aforementioned coefficients is thus variable over the irradiated plane; being high for parts of the body which are at all times irradiated by radiation in the central part of the spread and lower elsewhere.

If a particular region of the body is of special interest, then it is desirable that said particular region be disposed so that it is irradiated, at all times during the examination, by radiation in said central part of the spread. This is effected, as described in said U.S. Pat. application Ser. No. 493,403 by disposing the body so that the region of interest (assumed to be circular) is concentric with the axis about which the rotational scanning occurs. The spread of radiation is symmetrically disposed with respect to the axis of rotation, that is its median line intersects said axis.

It is not always convenient to shift the patient in such a manner, and it is one object of this invention to provide an alternative apparatus for examining a region of special interest in a body.

It is another object of this invention to provide scanning apparatus in which the median line of a planar spread of radiation, arranged to be scanned relative to a body about an axis perpendicular to the plane, is not concurrent with said axis throughout the scanning motion.

According to the invention there is provided scanning radiographic apparatus including a source of penetrating radiation, such as X-radiation, arranged to project a substantially planar spread of radiation, having a median line, through a body to be examined, and means for causing said source to effect a rotational scanning movement about an axis perpendicular to the plane of said spread, the arrangement being such that, over at least a substantial part of said rotational scanning movement, said median line and said axis are not concurrent. Preferably means are provided for adjusting the position of said spread relative to said body so that the said median line is initially disposed substantially centrally of a part of said body which is of special interest. Preferably also means are provided for imposing an additional movement upon said source whereby said median line is caused to pass substantially centrally through said part of said body for at least a substantial part of said rotational movement.

In order that the invention may be clearly understood and readily carried into effect, some embodiments thereof will now be described, by way of example only, with reference to the accompanying drawings of which:

FIG. 1 shows, in front elevational view, part of an apparatus in accordance with one example of the invention, and FIG. 2 shows, also in front elevational view, part of an apparatus in accordance with another example of the invention.

Referring now to FIG. 1, a body 1 is enclosed by a retaining ring 2 and may be surrounded in that ring by a suitable medium 3 which may be water, or a viscous or particulate material which absorbs X-radiation to substantially the same extent as does water, contained in one or more flexible bags. A source 4 is arranged to provide a substantially planar, fan-shaped spread of X-radiation 5 which is projected through the body towards detector means 6 which includes a detector array and corresponding collimators. Detector means 6 may include a simple bank of detectors, or, if desired, a more complex arrangement to provide correction for relative drift of the detectors. Compensating means 7 are also provided to equalise, so far as is practicable, the radiation paths across the circular section of ring 2. These may be as described in the aforementioned U.S. Pat. No. 3,937,963 or may be of carbon or aluminium having essentially the shape shown in the figure. The patient, together with items 2 and 3, is arranged to remain stationary during the examination. On the other hand, the source 4, detectors 6 and compensating means 7 are mounted on a scanning frame 8 which is arranged to rotate, around ring 2, about an axis 9 which is perpendicular to the spread 5 and is located at the centre of ring 2. The required rotational movement is provided, in this example by a set of teeth such as 10 which extend all around the circumference of frame 8 co-operating with a cog wheel 11 driven by a motor 12. Other means, such as a toothed belt drive may alternatively be provided. The motor 12 is mounted on a stationary mainframe 13 which can take any convenient form although it must, of course contain an aperture through which the body 1 can pass. Main frame 13 also carries three idler wheels 14, 15 and 16 which support the scanning frame 8. The wheels 14, 15 and 16 are flanged to restrict movement of the scanning frame 8 in a direction parallel to the axis 9.

In the arrangement shown in FIG. 1, although the source 4 and detector means 6 participate in the rotational motion of frame 8 about axis 9, they are required to orbit, in effect, about an axis in the centre of a region 17, of the body, which is of special interest. For this purpose the source and detector means are linked by a yoke 18, so that their motion is correctly related, and arranged to be capable of movement in relation to frame 8 as shown by the horizontal arrows. In this example the movement is allowed by bearings running in slots 19. They are allowed to move between the positions shown by solid and broken lines and the movement is such that the median line 20 of the spread 5 of radiation passes substantially centrally through region 17 for all orbital positions of frame 8. Thus it will be appreciated that over a substantial part of the rotational scanning movement the median line 20 does not intersect the axis 9. It will be realised that, for a steady orbital movement, the additional movement required to maintain the correct relation between the spread of radiation 5 and the body 1 is simple harmonic. Such a movement is provided in this example by a rotating bar 21, carrying a rod 22 which moves in a slot 23 in yoke 18. It will be apparent that steady rotation of bar 21 (by an electric motor, for example) about its end 24 remote from the yoke 18 will produce simple harmonic linear motion of the source 4 and detector means 6. Alternatively crank means or similar may be utilised to obtain the same effect. Bar 21 may be driven by the same motor as cog 11, by suitable gearing or similar, or may be maintained in a fixed relation with the orbital movement by servo means. The bar 21 rotates about an axis, through its end 24, parallel to axis 9.

It will be observed from FIG. 1 that the angular spread 5 of X-radiation is greater than that which would have been necessary to encompass the area 17. This is so in order that information can be obtained relating to the absorption characteristics of material in the part of the body surrounding the area 17 in response to beam paths of radiation which do not intersect the area 17. By means of this information it is possible to reduce inaccuracies, which would otherwise occur in the evaluation of the absorption coefficients for locations within the area 17, by allowing for the absorption characteristics of the material surrounding the area 17. The extent by which the angular extent of the spread 5 exceeds that which would have been required to irradiate area 17 depends on the accuracy with which it is required to evaluate the absorption coefficents in that area. In the present example the angular extent of spread 5 is only about twice as wide as that required to irradiate area 17, whereas in the arrangement to be described in relation to FIG. 2 the spread of X-radiation covers the entire breadth of the body in the irradiated plane. In either case, the resolution need not necessarily be the same for paths which pass outside the area of interest as it is for paths which pass through said area. Variation in resolution can be effected by spacing the detectors in the array 6 more widely for paths outside the area of interest than for paths through said area. Returning now to description of the FIG. 1 arrangement, the setting-up of the apparatus will now be described. It is desired in this example that the median line 20 of the spread 5 of X-radiation passes centrally through the area 17 of interest for all positions in the rotational movement of scanning frame 8 around the patient 1. If the centre of the area of interest lies on a horizontal line which intersects the axis 9, then it is merely necessary to adjust the position of the rod 22 along the bar 21 to provide a suitable initial relative position between the median line 20 and the area 17, this positioning being maintained during the scanning by the movement of the yoke 18 in response to the urging of the rod 22.

Should it be desired to inhibit the lateral movement of the yoke 18 when the yoke is in a position such as that shown in FIG. 1, i.e. with the median line 20 not concurrent with the axis 9, then it is necessary to prevent the rotation of the bar 21. This can be done, for example, by interrupting the electrical supplies to the motor which drives bar 21 or by means of a suitable clutch arrangement. In this case, the spread of radiation will irradiate either the whole body or an annular portion thereof when the scanning frame 8 executes its rotational scanning movement about axis 9. It will be appreciated that an annular region of the body will be irradiated if the extreme left hand beam of the spread 25 passes to the right of the axis 9 when the apparatus is in the rotational disposition shown in FIG. 1.

In the event that the centre of the area, such as 17, which is of special interest does not lie on the aforementioned horizontal line passing through axis 9, then the initial setting-up of the apparatus requires an additional movement, namely a rotational movement of bar 21 about its axis of rotation. The position of rod 22 along bar 21 and the rotational position of bar 21 are adjusted until the median line 20 of the spread 5 passes centrally through the region of interest and a perpendicular line drawn from the axis 9 to said median line intersects said median line at the centre of the region of interest. Once these positions have been fixed, the spread 5 is automatically maintained in the correct relationship to the area of interest throughout the scanning procedure.

In practice, the setting up can be automated by displaying a mimic diagram of the ring 2 and providing adjustable controls whereby an inner region corresponding to the area 17 can be moved relative thereto. The region corresponding to area 17 is adjusted, by manipulating the controls, so that it is located in a position, relative to the representation of ring 2, corresponding to the area of special interest in the body and the act of so positioning said region develops control signals which are fed to the drive motor for bar 21 and to a suitable driving means (not shown) for moving rod 22 along bar 21 so that these components automatically assume the desired dispositions before the start of the rotational scan.

An alternative embodiment of the invention will now be described with reference to FIG. 2, in which components common to FIG. 1 are identified by the same reference numbers.

The fundamental difference between the arrangements of FIGS. 1 and 2 is that the rotating bar 21 and rod 22 are replaced by a reciprocable motor 25 which drives a toothed belt 26 by way of a drive wheel 27. The belt 26 also passes over an undriven idler wheel 28 and it carries a source 4 of X-radiation, which is secured thereto by means of a bracket 29, and also a yoke 30 which is secured to the source 4 and supports the detector/collimator array 6. The yoke 30 can move laterally, in response to motion of the belt 26, on a pair of runners 31, 32 formed on the scanning frame 8. The belt 26 also carries, on the opposite run to the source 4, a counterbalance weight 33 which moves in opposition to the source and maintains a proper weight distribution relative to the rotational axis 9 of the scanning frame 8.

Frame 8 is also formed with an annular graticule 34 which contains alternate matt and reflective markings by means of which a photocell lamp/detector unit 35, which remains fixed whilst the rotation of frame 8 carries the graticule markings past it, can monitor the progress of the rotational scan and produce, in known manner, timing pulses indicative of such progress. Of course, the graticule 34 need not be formed on the frame 8. It could alternatively be provided on the shaft of the motor 12 which drives the gear wheel 11 or on one of the idler wheels 13, 14 or 15.

In operation of the arrangement of FIG. 2, the co-ordinates of the centre of a circular area 17 of special interest are supplied to a circuit 36, which preferably comprises part of a digital computer, and the circuit 36 is arranged to produce a driving signal for the reciprocating motor 25 which achieves the desired object of maintaining the median line 20 of the spread 5 and the perpendicular to said median line from the axis 9 concurrent at the centre of area 17 throughout the rotational scanning movement of the frame 8 around the body.

As mentioned in relation to FIG. 1, the detectors outside those which receive radiation from a central portion 37 of the spread 5 can be more widely spaced than those embraced by the portion 37. Whether or not this is the case, each detector feeds a respective preprocessing circuit such as the one shown in a dashed rectangle 38. Signals derived from a detector, which may for example, comprise a scintillator crystal and a photomultiplier tube or a scintillator crystal and a photodiode, are applied first to an amplifier 39. Each amplifier such as 39 feeds a respective integrator such as 40; the integrators being read and reset periodically by means of the timing pulses produced by the photocell unit 35. Each integrator feeds a respective analogue-to-digital converter circuit 41 and thence a log converter circuit 42. The outputs of all the circuits such as 42 are fed, together with the timing pulses from photocell 35 and the information concerning the coordinates of the centre of the area 17 into a digital computer 43 which includes the aforementioned circuit 36.

The signals applied to the computer 43 from the circuits 42 are processed, for example in the manner described in U.S. Pat. No. 3,924,129 preferably after having first been sorted into signals relating to sets of substantially parallel beam paths through the body 1 in the manner described in U.S. application Ser. No. 544,799 filed on Jan. 28, 1975. The processing is effective to evaluate the absorption (or transmission) coefficient, with respect to the X-radiation used, at least at a number of small elements distributed over the area 17. These coefficients are displayed on a suitable cathode ray tube 44, the evaluated coefficients being applied to the tube 44 by way of window width and level control circuits 45, of the kind described in U.S. Pat. No. 3,778,614 whereby the total dynamic range of the displayed coefficients and the absolute level of the centre of the dynamic range can be adjusted, to enable different aspects of the body, e.g. fatty tissue, bone etc. to be displayed.

If desired, circuit 36 can be merely a store which holds, say, one hundred programmes for motor 25, each associated with a respective centre point for the area 17. When the co-ordinates of a desired centre point are applied to the store, the desired programme is executed. In this case, the control circuits associated with the aforementioned mimic diagram can be such that the centre of the region corresponding to the area 17 can only occupy positions which correspond to locations for which a programme has been stored.

The compensating means corresponding to those indicated at 7 in FIG. 1 have been omitted from FIG. 2 for clarity but they may, of course, be provided if desired in an apparatus of the kind shown in FIG. 2.

An additional difference between the arrangements shown in FIGS. 1 and 2 resides in the manner of supporting the patient's body 1. In FIG. 2, the patient's body is supported on a bed 46 of unitary construction and semi-cylindrical form, with packing material 3, as before, used to fill gaps between the body and the bed. The patient is restrained in the bed 46 by means of one or more straps such as that shown at 47. These straps are preferably secured to the sides of the bed 46 as shown.

It will be evident that the patient supporting means of FIG. 2 can be used with the other components of FIG. 1, and vice versa.

Other embodiments of the invention will be apparent to those skilled in the art of radiography, and it is to be understood that the embodiments described above are exemplary only and are not intended to limit the scope of the claims.

In an alternative technique, a large ring is made slidably movable relative to the main frame of the apparatus, so that the ring can be physically moved to adopt a position in which it is coaxial with the centre of the particular region of interest in the patient's body. The source of radiation and the detector devices are mounted on a suitable frame, which is preferably substantially square in shape; this frame being rotatable about a fixed centre of rotation relative to the apparatus. The frame is formed with flange members on two opposite sides thereof, which members are arranged to remain in tangential contact with opposite sides of said ring; the square frame being slidably movable relative to the rotating parts of the apparatus so that it can be physically displaced by the action of the flanges on the stationary ring so as to cause the radiation to be always directed through said region of particular interest. This arrangement has a disadvantage in that the relative spacing between the source and the region of interest can change during the rotational scan, and thus the distribution of radiation beam paths through said region can change accordingly. The degree of change is dependent upon the displacement of the centre of the ring from the fixed centre of rotation of the apparatus, and, if this embodiment is used, it is necessary to allow for such changes in the computation of said absorption coefficients.

What is claimed is:

1. Scanning radiographic apparatus including a source of penetrating radiation, such as X-radiation, arranged to project a substantially planar spread of radiation, having a median line, through a body to be examined, a support for said source, means for causing said support to effect a rotational scanning movement about an axis perpendicular to the plane of said spread so that said median line assumes, in the course of said rotational scanning movement, in sequence a number of different angular orientations with respect to the body and in the plane of said spread of radiation and means for causing said median line, in at least a substantial number of its different orientations and throughout the time the median line assumes those orientations, to remain in a region of said body away from said axis and not to intersect said axis.

2. Apparatus according to claim 1 including means for adjusting the position of said spread relative to said body so that the said median line is initially disposed substantially centrally of a selected part of said body.

3. Apparatus according to claim 2 wherein the causing means include means for imposing a relative movement on said support and source to cause said median line to pass substantially centrally through said selected body part over at least a substantial angular part of said rotational movement.

4. Apparatus according to claim 1 wherein said spread of radiation is of fan-like form.

5. Apparatus according to claim 1 including detector means disposed to receive radiation emerging from said body.

6. Apparatus according to claim 5 including means for processing output signals provided by said detector means to evaluate absorption coefficients at a plurality of elements of said body in the plane of said spread of radiation.

7. Apparatus according to claim 5 including a yoke linking said source to said detector means.

8. A method of examining part of a body by means of X-radiation, comprising the steps of projecting radiation, from an X-ray source on a support, through said body in a plane along a spread of radiation having a median line, rotating the support about an axis perpendicular to the said plane so as to irradiate the body from a plurality of different directions, and positioning the X-ray source relative to the support so that in the course of said rotation, said median line assumes, in sequence, a number of different angular with respect to the body and in the plane of said spread of radiation and the median line, in at least a substantial number of its different orientations and throughout the time the median line assumes those orientations, remains in a region of said body away from said axis and does not intersect the axis.

9. A computerized axial tomographic device comprising:
means for supporting a patient at a fixed position intersected by a plane of interest;
means for generating penetrating radiation travelling substantially within said plane and intersecting said fixed position and means for detecting the radiation emerging from said fixed position after travelling along said plane;
means for orbiting at least the generating means to cause the detecting means to detect said radiation from a plurality of different directions over an angular span of at least about 180°, the radiation from each direction having a median line; and
said orbiting means comprising a yoke supporting at least the generating means and means for orbiting the yoke about a selected axis transverse to said plane and for moving at least the generating means relative to the yoke to cause said median lines to intersect in a region of the plane which is misaligned with said selected axis at least over a substantial portion of said orbiting of the yoke.

10. A computerized axial tomographic device as in claim 9, including means for adjusting the position of at least the generating means relative to the yoke, prior to orbiting, for selecting said region.

11. A computerized axial tomography device as in claim 9 wherein the generating means include means for shaping the radiation into fan-shaped planar spreads of radiation travelling substantially within said plane of interest and traversing areas of the patient outside said region, and including means coupled to the detecting means to derive therefrom measurement signals determined by the amounts of radiation arriving at the detecting means along said paths, and for processing said measurement signals to derive a representation of properties of the matter relative to said radiation within said plane of interest through the patient, said representation having greater detail within said region and lesser detail outside said region.

12. A medical radiology method comprising the steps of:
generating penetrating radiation travelling substantially within a plane of interest traversing a patient disposed at a fixed position by a radiation source on a support disposed outside the patient; and
orbiting the support about an axis intersecting said plane of interest within the patient body and moving the source relative to the support in the course of said orbiting to cause the median line of the radiation from said source to take a succession of dispositions which intersect substantially at a region offset from said orbiting axis of the support.

* * * * *

UNITED STATES PATENT AND TRADEMARK OFFICE
CERTIFICATE OF CORRECTION

PATENT NO. : 4,114,040
DATED : September 12, 1978
INVENTOR(S) : GODFREY NEWBOLD HOUNSFIELD It is certified that error appears in the above-identified patent and that said Letters Patent are hereby corrected as shown below:

Column 7, line 30 (Claim 8), after "angular" and before "with" insert -- orientations --.

Signed and Sealed this

Tenth Day of April 1979

[SEAL]

Attest:

RUTH C. MASON
Attesting Officer

DONALD W. BANNER
Commissioner of Patents and Trademarks